United States Patent [19]
Nicoll et al.

[11] Patent Number: 5,188,831
[45] Date of Patent: Feb. 23, 1993

[54] SUNSCREENS CONTAINING BOTH WATER AND OIL DISPERSIBLE TITANIUM DIOXIDE PARTICLES

[75] Inventors: Gregg A. Nicoll, Dumont, N.J.; Ann C. Ojo-Osagie, Bedford; Ian R. Scott, Wellingborough, both of England

[73] Assignee: Chesebrough-Pond's USA Co., Division of Conopco, Inc., Greenwich, Conn.

[21] Appl. No.: 698,432

[22] Filed: May 10, 1991

[30] Foreign Application Priority Data

May 10, 1990 [GB] United Kingdom ............... 9010526

[51] Int. Cl.$^5$ .................................... A61K 7/45
[52] U.S. Cl. ................................. 424/401; 424/59; 424/63; 424/69
[58] Field of Search .................... 424/59, 63, 69, 401

[56] References Cited

U.S. PATENT DOCUMENTS

| | | |
|---|---|---|
| 4,119,712 | 10/1978 | Goldner et al. ............... 424/69 X |
| 5,008,101 | 4/1991 | Klimisch et al. ............... 424/59 |

FOREIGN PATENT DOCUMENTS

| | | |
|---|---|---|
| 3824999 | 7/1988 | Fed. Rep. of Germany . |
| 59-172415 | 9/1984 | Japan . |
| 1417574 | 5/1972 | United Kingdom . |
| 2184356 | 12/1986 | United Kingdom . |
| 2206282 | 1/1989 | United Kingdom . |
| 2206339 | 1/1989 | United Kingdom . |
| 2211736 | 7/1989 | United Kingdom . |
| 2217987 | 11/1989 | United Kingdom . |

Primary Examiner—Thurman K. Page
Assistant Examiner—Robert H. Harrison
Attorney, Agent, or Firm—Milton L. Honig

[57] ABSTRACT

A composition for topical application to human skin to provide protection from excessive exposure to ultraviolet rays, comprises an effective amount of a sunscreen comprising water-dispersible ultrafine titanium dioxide and oil-dispersible ultrafine titanium dioxide, together with a cosmetically acceptable vehicle for the sunscreen.

9 Claims, No Drawings

SUNSCREENS CONTAINING BOTH WATER AND OIL DISPERSIBLE TITANIUM DIOXIDE PARTICLES

FIELD OF THE INVENTION

The invention relates to compositions for topical application to human skin to provide enhanced protection from the damaging effects of sunlight.

BACKGROUND AND PRIOR ART

The damaging effects of sunlight on human skin have been observed since time immemorial and many remedies have been proposed to protect the skin from this damage.

In general terms, harmful ultra-violet (UV) rays, particularly those originating from sunlight, which penetrate the upper atmosphere and reach the earth's surface, can be classified into:

i. the energy-rich UV-B rays (290–320 nm wavelength) which possess an intense physiopathological activity on the skin; these are absorbed just above the dermis and they are responsible for erythema and skin pigmentation, and ii. UV-A rays (320–400 nm wavelength) which penetrate deeper into the skin (to the dermis and beyond). Their energy is much lower and the photobiological effects they cause are much more long term in nature, for example, they accelerate skin ageing.

Certain organic substances (sunscreens) whose molecules *absorb* the harmful ultra-violet rays have been proposed for use in mitigating the deleterious effects of ultra-violet radiation.

Some of these substances absorb more effectively in UV-A range thereby providing filtering of UV radiation in this range, while others are more effective in the UV-B range.

A common problem exists, however, whatever the choice of organic sunscreen, for protection from whichever wavelength of ultra-violet radiation, and this is that physiological damage to the body can occur, following topical application of these sunscreens in quantities necessary to provide effective filtering of harmful ultra-violet radiation. Even those organic sunscreens that are believed to be safe to use in this way, necessarily have safety limits imposed, based on the quantity applied to the skin, which can result in only moderate to poor protection from harmful ultra-violet radiation.

Certain inorganic substances have also been proposed for use as sunscreens which physically block exposure of the skin to ultra-violet rays. Notable of these is titanium dioxide having a very small particle size This grade of titanium dioxide, designated ultrafine $TiO_2$, affords a good degree of sun blocking potential without the unacceptable skin whitening experienced with the normal pigmentary grade (particle size >300 nm). For example, in DE-A-3824999 (The Boots Company PLC), it is proposed to use titanium dioxide with a mean primary particle size of <100 nm in a water-in-oil emulsion as a sunscreen preparation. This reference also suggests that organic sunscreen agents, such as p-aminobenzoic acid and esters thereof, methoxycinnamate, benzophenone, dibenzoylmethanes or salicylates can also be included to improve protection.

In spite of this, and other prior proposals, there still exists a need for a highly efficient and thoroughly safe sun protection composition which has a wide spectrum of protection (i.e. both UV-A and UV-B) in the UV region.

SUMMARY OF THE INVENTION

Applicants have now discovered that by the use of two different types of ultrafine titanium dioxide in a composition adapted for use topically on the skin, synergistically enhanced protection from ultra-violet rays can be attained.

DEFINITION OF THE INVENTION Accordingly, the invention provides a composition for topical application to human skin to provide protection from excessive exposure to ultra-violet rays, which comprises:

a. an effective amount of a sunscreen comprising a mixture of water-dispersible ultrafine titanium dioxide and oil-dispersible ultrafine titanium dioxide; and b. a cosmetically acceptable vehicle for the sunscreen.

DISCLOSURE OF THE INVENTION

The invention is concerned with a composition suitable for topical application to human skin to provide protection from excessive exposure to ultra-violet rays over a wide range of wave lengths, notably covering both the UV-A and the UV-B ranges. The composition of the invention comprises a special mixture of two different grades of ultrafine titanium dioxide which are conveniently dispersed or distributed in a cosmetically acceptable vehicle. Depending upon the nature of the composition, other skin benefit materials and/or cosmetic adjuncts can optionally be present.

THE TITANIUM DIOXIDE

The composition according to the invention comprises ultrafine titanium dioxide in two forms, namely water-dispersible titanium dioxide and oil-dispersible titanium dioxide.

Water-dispersible titanium dioxide, in accordance with the invention, is ultrafine titanium dioxide, the particles of which are uncoated or which are coated with a material to impart a hydrophilic surface property to the particles. Examples of such materials include aluminum oxide and aluminum silicate.

Oil-dispersible titanium dioxide, in accordance with the invention, is ultrafine titanium dioxide, the particles of which exhibit a hydrophobic surface property, and which, for this purpose, can be coated with metal soaps such as aluminium stearate, aluminum laurate or zinc stearate, or with organosilicone compounds.

By "ultrafine titanium dioxide" is meant particles of titanium dioxide having an average particle size of less than 100 nm, preferably from 10 to 40 nm and most preferably from 15 to 25 nm.

It has accordingly been discovered that by topical application to the skin of a mixture of both water-dispersible ultrafine titanium dioxide and oil-dispersible ultrafine titanium dioxide, synergistically enhanced protection of the skin against the harmful effects of both UV-A and UV-B rays is achievable. Evidence to demonstrate this effect will be given later in this specification.

It is believed that this unexpected benefit is due to the deposition of each type of titanium dioxide on different regions of the skin surface, water-dispersible titanium dioxide being preferentially retained by hydrophilic regions of the skin's surface, while oil-dispersible titanium dioxide is retained preferentially by hydrophobic regions of the skin's surface. The combined overall effect is that more efficient physical coverage of the skin's surface is attainable and this can be demonstrated by measurement of the Sun Protection Factor (SPF), a property of sunscreens, whose measurement will be described and demonstrated later in this specification. In order to achieve the enhanced, synergistic benefit, as herein described, the weight ratio of water-dispersible titanium dioxide to oil-dispersible titanium dioxide should be from 1:4 to 4:1, preferably from 1:2 to 2:1 and ideally about equal weight proportions.

The total amount of titanium dioxide in the composition according to the invention is from 1 to 25%, preferably from 2 to 10% and ideally from 3 to 7% by weight of the composition. Experimental evidence has shown that the synergistic benefit, as described herein, is most pronounced at a total titanium dioxide level of about 5% by weight, and is lost when the titanium level reaches 10% by weight, equal proportions of the water-dispersible and oil-dispersible forms of titanium dioxide being used in this experiment. Likewise, no significant sun protection benefit is shown when the total level of titanium dioxide falls below 1% by weight.

THE COSMETICALLY ACCEPTABLE VEHICLE

The composition according to the invention also comprises a cosmetically acceptable vehicle to act as a dilute, dispersant or carrier for other materials present in the composition, so as to facilitate their distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminum silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the emulsion.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lipophilic balance (HLB) of the emulsifier employed.

OIL OR OILY MATERIAL

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

EMULSIFIER

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl | Brij 30 | 9.7 |

TABLE 1-continued

| Chemical Name of Emulsifier | Trade Name | HLB Value |
|---|---|---|
| ether | | |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

WATER

The composition of the invention can also comprise water, usually up to 80%, preferably from 5 to 80% by volume.

SILICONE SURFACTANT

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

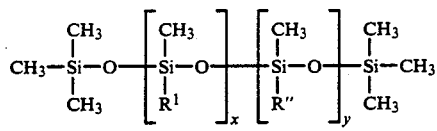

where the groups R' and R" are each chosen from —H, $C_{1-18}$ alkyl and

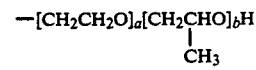

a has a value of from 9 to 115,
b has a value of from 0 to 50,
x has a value of from 133 to 673,
y has a value of from 25 to 0.25.

Preferably, the dimethyl polysiloxane polymer is one in which:

a has a value of from 10 to 114
b has a value of from 0 to 49
x has a value of from 388 to 402
y has a value of from 15 to 0.75 one of groups R' and R" being lauryl, and the other having a molecular weight of from 1000 to 5000.

A particularly preferred dimethyl polysiloxane polymer is one in which:

a has the value 14
b has the value 13
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

ORGANIC SUNSCREENS

The emulsion of the invention optionally can comprise an organic sunscreen further to enhance the benefit of the emulsion in providing protection from the harmful effects of excessive exposure to sunlight.

As has already been stated, some organic sunscreens can be harmful to health if applied topically to the skin at a concentration sufficient to screen out effectively radiation from either the UV-A range or the UV-B range. The presence however, of ultrafine titanium dioxide, which can provide a broad spectrum of protection, enables a lower than usual amount of organic sunscreen materials to be used to "top-up" the overall Sun Protection Factor of the emulsion to an exceptionally high level, without the risk of causing the type of skin damage or other health problems that can be associated with the use of higher levels of organic sunscreen materials alone.

In view of this, a relatively small amount of organic sunscreen optionally can be incorporated into the emulsion of the invention.

Examples of suitable organic sunscreens, when required, include those set out in Table 2 below, and mixtures thereof.

TABLE 2

| CTFA Name | Trade Name | Supplier |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The emulsion of the invention can accordingly comprise from 0.1 to 10%, preferably from 1 to 5% by weight of an organic sunscreen material.

OTHER ORGANIC SUNSCREENS

The emulsion of the invention optionally can comprise an inorganic sunscreen in addition to ultrafine titanium dioxide as herein defined.

Examples of other inorganic sunscreens include:
zinc oxide, having an average particle size of from 1 to 300 nm,
iron oxide, having an average particle size of from 1 to 300 nm,
silica, such as fumed silica, having an average particle size of from 1 to 100 nm.

It should be noted that silica, when used as an ingredient in the emulsion according to the invention can provide protection from infra-red radiation.

OTHER COSMETIC ADJUNCTS

Examples of conventional adjuncts which can optionally be employed include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene glycol, such as PEG 200–600; buffers, such as lactic acid together with a base such as triethanolamine or sodium hydroxide; waxes, such as beeswax, ozokerite wax, paraffin wax: plant extracts, such as Aloe vera, cornflower, witch hazel, elderflower, cucumber; thickeners; activity enhancers; colourants; and perfumes. Cosmetic adjuncts can form the balance of the composition.

USE OF THE COMPOSITION

The composition according to the invention is intended primarily as a sun care product for topical application to human skin to protect exposed skin from the harmful effects of excessive exposure to sunlight.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

METHOD FOR DETERMINATION OF SUN PROTECTION FACTOR (SPF) IN VITRO

The method for the in vitro SPF determination of the emulsion of the invention involves the spectrophotometric scanning of stratum corneum between 400 nm and 290 nm utilising a Perkin Elmer Lamba 17 spectrophotometer equipped with a diffuse transmission detection system.

Guinea pig stratum corneum is used in place of human skin and the following procedure is followed.

i. Guinea pig stratum corneum is isolated as fine sheets from guinea pig skin and air dried.
ii. A piece of the stratum corneum is applied to the outer surface of a 0.5 cm quartz cuvette using a drop of distilled water to seal the stratum corneum uniformly to the quartz surface.
iii. The quartz cuvette carrying the piece of stratum corneum is placed in the light path of the spectrophotometer which for this purpose is fitted with a fluorescence cut-off filter. This filter eliminates the autofluorescence of the stratum corneum and filters out all transmissions above 400 nm.
iv. The stratum corneum is scanned from 290 to 400 nm and the spectrum obtained is saved as the control.
v. The cuvette with stratum corneum is removed from the spectrophotometer and the test material (i.e. sunscreen) is applied to the stratum corneum at the rate of 1.5 $\mu l/cm^2$, in accordance with German DIN protocol, and rubbed uniformly across the entire surface of the skin using the finger fitted with a finger stall.
vi. The applied sunscreen material is allowed to stand for 5 minutes at room temperature (20° C.) to enable it to dry, and then the sample is rescanned in the spectrophotometer as before from 290 to 400 nm. This spectrum is saved as the test spectrum. No spectral absorbance changes were observed with drying times between 2 and 15 minutes; the 5 minute drying time was therefore adopted as standard.
vii. The control spectrum is subtracted from the test spectrum to provide the spectral absorbance of the test sample of sunscreen material and this absorbence is converted to transmission.
viii. The in vitro Sun Protection Factor (SPF) is finally calculated from the transmission measurements as described by Diffey et al, in a paper entitled: "A new substrate to measure sunscreen protection factors throughout the ultra-violet spectrum" in J. Soc. Cosmet. Chem. 40. 127–133 (May/June 1989); see especially page 130.

EVIDENCE TO DEMONSTRATE THE SYNERGISTICALLY ENHANCED PROTECTION OF SKIN AGAINST ULTRA-VIOLET RAYS WITH BOTH WATER-DISPERSIBLE AND OIL-DISPERSIBLE ULTRAFINE TITANIUM DIOXIDE

In this experiment, the Sun Protection Factor (SPF) of water-dispersible titanium dioxide an oil-dispersible titanium dioxide were each measured separately and as a mixture using the German DIN technique, as published in "Deutsches Institut für Normung." DIN 67 50I December 1985.

The formulations in this experiment were as follows:

| Ingredients | Formulation No. | | |
|---|---|---|---|
| | 1 | 2 | 3 |
| Polyoxyethylene (2) stearyl alcohol | 3.0 | 3.0 | 3.0 |
| Polyoxyethylene (21) stearyl alcohol | 2.0 | 2.0 | 2.0 |
| Cetyl alcohol | 1.5 | 1.0 | 1.5 |
| Paraffin, soft white | 1.5 | 1.5 | 1.5 |
| Dimethicone polydimethylsilicone | 5.0 | 5.0 | 5.0 |
| Liquid paraffin | 8.0 | 20.0 | 8.0 |
| Glycerin | 2.0 | 2.0 | 2.0 |
| Titanium dioxide oil dispersible | — | 5.0 | 2.5 |
| Titanium dioxide water dispersible | 5.0 | — | 2.5 |

| Ingredients | Formulation No. | | |
|---|---|---|---|
| | 1 | 2 | 3 |
| Preservative | 0.5 | 0.5 | 0.5 |
| Water | 71.5 | 60.0 | 71.5 |

The results obtained are set out in Table 3 below.

TABLE 3

| Formulation No. | Titanium dioxide (TiO$_2$) | % w/w | SPF |
|---|---|---|---|
| 1 | W/D TiO$_2$ | 5.0 | 4.1 |
| 2 | O/D TiO$_2$ | 5.0 | 4.6 |
| 3 | W/D + O/D TiO$_2$ | 2.5 + 2.5 | 5.7 |

W/D is water-dispersible
O/D is oil-dispersible

The results shown in Table 3 confirm that a proportionally greater benefit in terms of SPF was achieved when the total amount of titanium dioxide in the test formulation was 5% comprising equal weights of each type of titanium dioxide, than when either water-dispersible or oil-dispersible titanium dioxide were each used at the 5% w/w level. This suggested an unexpected (synergistic) response for the mixture.

Three further formulations (1A, 2A and 3A) each containing twice the quantity of titanium dioxide, were also tested in a similar manner. The formulations were otherwise similar to Formulations 1,2 and 3 above, except that the amount of water was reduced by 5% by weight to compensate for a corresponding increase in titanium dioxide.

The results obtained are set out in Table 4 below.

TABLE 4

| Formulation No. | Titanium dioxide (TiO$_2$) | % w/w | SPF |
|---|---|---|---|
| 1A | W/D TiO$_2$ | 10.0 | 8.1 |
| 2A | O/D TiO$_2$ | 10.0 | 12.3 |
| 3A | W/D + O/D TiO$_2$ | 5.0 + 5.0 | 10.5 |

The results shown in Table 4 apparently show a lack of synergy between the two forms of TiO$_2$:—this is in fact not the case. It is not correct to assume that the average of the SPF with water dispersible TiO$_2$ (8.1) and that with oil dispersible TiO$_2$ (12.3) is the arithmetical mean (10.2). The true average is obtained by converting SPF into an absorbance figure of log ($^1$/SPF), averaging the absorbance figures and reconverting to an average SPF thus:

$$\frac{1}{\text{average SPF}} = 10^{[\frac{(\log 1/SPF_1 + \log 1/SPF_2)}{2}]}$$
$$= 9.98$$

Thus the mixture of the two types of TiO$_2$ gives an unexpected additional SPF of 10.5−9.98=0.5.

These results show that mixtures of O/D and W/D TiO$_2$ give unexpectedly greater SPF than expected by averaging the light absorbances of the two components separately. The effect is proportionately greater at total TiO$_2$ concentrations of 5% than at 10% but the effect is present at both concentrations.

EXAMPLES

The invention is further illustrated by the following examples; in each formulation, the titanium dioxide employed was ultrafine titanium dioxide having a mean particle size of from 15 to 25 nm.

EXAMPLE 1

This example illustrates a lotion according to the invention.

| Ingredient | % w/w |
|---|---|
| silicone surfactant | 10.00 |
| volatile siloxane | 14.00 |
| mineral oil | 1.50 |
| titanium dioxide (water-dispersible) | 2.50 |
| titanium dioxide (oil-dispersible) | 2.50 |
| 2-hydroxy octanoic acid | 1.00 |
| 2-hydroxy propanoic acid | 5.00 |
| butylene glycol | 10.00 |
| sodium chloride | 2.00 |
| l-proline | 0.10 |
| neutralizing agent | qs |
| preservative | qs |
| perfume | qs |
| water | qs |

EXAMPLE 2

This example illustrates a fluid cream according to the invention.

| Ingredient | % w/w |
|---|---|
| volatile siloxane (DC 345) | 8.20 |
| silicone surfactant (DC 3225C) | 12.00 |
| petroleum jelly | 0.50 |
| mineral oil | 1.50 |
| Parsol MCX (octyl methoxycinnamate) | 3.00 |
| titanium dioxide (oil-dispersible) | 2.00 |
| titanium dioxide (water-dispersible) | 2.00 |
| sodium chloride | 2.00 |
| butylene glycol | 10.00 |
| l-proline | 0.10 |
| 2-hydroxy octanoic acid | 1.00 |
| 2-hydroxy propanoic acid | 5.00 |
| neutralizing agent | qs |
| preservative | qs |
| perfume | qs |
| water | qs |

EXAMPLE 3

This example illustrates a cream according to the invention.

| Ingredient | % w/w |
|---|---|
| volatile siloxane (DC 345 Fluid) | 8.2 |
| silicone surfactant (DC 3225C) | 12.0 |
| mineral oil | 1.5 |
| petroleum jelly | 0.5 |
| Parsol MCX (octyl methoxycinnamate) | 1.5 |
| titanium dioxide (oil-dispersible) | 1.0 |
| titanium dioxide (water-dispersible) | 1.0 |
| 2-hydroxyoctanoic acid | 1.0 |
| 2-hydroxypropanoic acid | 5.0 |
| sodium chloride | 2.0 |
| butylene glycol | 10.0 |
| l-proline | 0.10 |
| neutralizing agent (aqueous phase to 4.5) | q.s. |
| preservative | q.s. |
| perfume | q.s. |
| water | to 100 |

EXAMPLE 4

This example illustrates a lotion according to the invention.

| Ingredient | % w/w |
|---|---|
| silicone surfactant (DC 3225C) | 10.00 |
| volatile siloxane (DC 345) | 14.00 |
| mineral oil | 1.50 |
| Parsol MCX | 3.00 |
| titanium dioxide (oil-dispersible) | 2.00 |
| titanium dioxide (water-dispersible) | 2.00 |
| butylene glycol | 10.00 |
| sodium chloride | 2.00 |
| l-proline | 0.10 |
| 2-hydroxy octanoic acid | 1.00 |
| 2-hydroxy propanoic acid | 5.00 |
| neutralizing agent | qs |
| perfume | qs |
| preservative | qs |
| water | qs |

EXAMPLE 5

This example illustrates a sunscreen cream in accordance with the invention.

| Ingredient | % w/w |
|---|---|
| Polyoxyethylene (2) stearyl alcohol | 3 |
| Polyoxyethylene (21) stearyl alcohol | 2 |
| cetyl alcohol | 1.5 |
| soft white paraffin | 1.5 |
| silicone fluid 200 | 5 |
| liquid paraffin | 8 |
| glycerin | 2 |
| preservatives | 0.5 |
| titanium dioxide (water-dispersible) | 2.5 |
| titanium dioxide (oil-dispersible) | 2.5 |
| water | to 100 |

EXAMPLE 6

This example also illustrates a sunscreen cream in accordance with the invention.

| Ingredients | % w/w |
|---|---|
| cetyl dimethicone copolyol | |
| cetyl dimethicone | * 5 |
| polyglyceryl-3-oleate | |
| hexyl laurate | |
| isopropyl myristate | 13.5 |
| beeswax | 3 |
| silicone fluid 200 | 5 |
| preservatives | 0.5 |
| titanium dioxide (water-dispersible) | 2.5 |
| titanium dioxide (oil-dispersible) | 2.5 |
| water | to 100 |

*Available is ABIL W508 ex Goldschmidt

EXAMPLE 7

This example illustrates a lotion according to the invention.

| Ingredient | % w/w |
|---|---|
| silicone surfactant | 10.00 |
| volatile siloxane | 14.00 |
| mineral oil | 1.50 |
| ultrafine titanium dioxide (water-dispersible) | 2.50 |
| ultrafine titanium dioxide (oil-dispersible) | 2.50 |
| 2-hydroxy octanoic acid | 1.00 |
| 2-hydroxy propanoic acid | 5.00 |
| butylene glycol | 10.00 |
| sodium chloride | 2.00 |
| amino acid | 0.10 |
| neutralizing agent | qs |

| Ingredient | % w/w |
| --- | --- |
| preservative | qs |
| perfume | qs |
| water | qs |

SPF Data

The lotion when tested in vitro produced an SPF of 10.0 (± standard error of the mean (SEM)=0.7).

COMPARATIVE EXPERIMENTS

Experiment 1

The formulation shown in Example 7 was modified by omitting oil-dispersible ultrafine titanium dioxide (2.5% w/w), and replacing it with an equal quantity of additional water-dispersible titanium dioxide, so that the formulation now contained a total of 5% w/w of water-dispersible ultrafine titanium dioxide. The formulation of Experiment 1 was accordingly as follows:

| Ingredient | % w/w |
| --- | --- |
| silicone surfactant | 10.00 |
| volatile siloxane | 14.00 |
| mineral oil | 1.50 |
| ultrafine titanium dioxide (water-dispersible) | 5.00 |
| 2-hydroxy octanoic acid | 1.00 |
| 2-hydroxy propanoic acid | 5.00 |
| butylene glycol | 10.00 |
| sodium chloride | 2.00 |
| amino acid | 0.10 |
| neutralizing agent | qs |
| preservative | qs |
| perfume | qs |
| water | qs |

SPF Data

The lotion when tested in vitro produced an SPF of 7.8 (± standard error of the mean (SEM)=0.3).

Experiment 2

The formulation shown in Example 7 was again modified by omitting this time water-dispersible ultrafine titanium dioxide (2.5% w/w) and replacing it with an equal quantity of added oil-dispersible titanium dioxide, so that the formulation now contained a total of 5% w/w oil-dispersible ultrafine titanium dioxide. The formulation of experiment 2 was accordingly as follows:

| Ingredient | % w/w |
| --- | --- |
| silicone surfactant | 10.00 |
| volatile siloxane | 14.00 |
| mineral oil | 1.50 |
| ultrafine titanium dioxide (oil-dispersible) | 5.00 |
| 2-hydroxy octanoic acid | 1.00 |
| 2-hydroxy propanoic acid | 5.00 |
| butylene glycol | 10.00 |
| sodium chloride | 2.00 |
| amino acid | 0.10 |
| neutralizing agent | qs |
| preservative | qs |
| perfume | qs |
| water | qs |

SPF Data

The lotion when tested in vitro produced an SPF of 7.9 (± standard error of the mean (SEM)=0.4).

CONCLUSION

When comparing the SPF data of the Example 7 formulation, in accordance with the invention, with those of the Experiments of 1 and 2 formulations, which contain either water-dispersible ultrafine titanium dioxide or oil-dispersible ultrafine titanium dioxide, and which are accordingly not in accordance with the invention, it is apparent that for the same quantity of titanium dioxide present in each of the formulations, i.e. 5% by weight, the SPF value for Example 7 formulation is significantly greater than the SPF values of either Experiment 1 or Experiment 2.

The demonstrates the superiority of combining in the same formulation the proportion of oil-dispersible ultrafine titanium dioxide with a proportion of water-dispersible ultrafine titanium dioxide.

We claim:

1. A composition for topical application to human skin to provide protection from excessive exposure to ultra-violet rays, which comprises:
   (a) an effective amount of a sunscreen comprising a mixture of water-dispersible titanium dioxide exhibiting a hydrophilic surface and an oil-dispersible titanium dioxide exhibiting a hydrophobic surface, each of said titanium dioxides having an average particle size of less than 100 nm in total amount said titanium dioxides being present from 3 to 7% by weight and said water-dispersible and oil-dispersible titanium dioxides being present in a respective ratio of 1:2 to 2:1; and
   (b) a cosmetically acceptable vehicle for said sunscreen.

2. The composition according to claim 1, which is an emulsion.

3. The composition according to claim 1, which further comprises a silicone oil.

4. The composition according to claim 1, which further comprises a silicone surfactant.

5. The composition according to claim 1, which further comprises an organic sunscreen.

6. The composition according to claim 5, wherein the organic sunscreen is octyl methoxycinnamate.

7. A method for protecting human skin from the harmful effects of excessive exposure to ultra-violet rays, which comprise the step of applying to the skin an effective amount of the composition according to claim 1.

8. The composition according to claim 1 wherein said total amount of titanium dioxide is about 5%.

9. The composition according to claim 8 wherein said ratio is about 1:1.

* * * * *